United States Patent [19]

Kaplan

[11] 4,074,709
[45] Feb. 21, 1978

[54] METHOD AND DEVICE FOR FACILITATING DOUBLE-CONTRAST STUDIES OF THE UPPER GASTROINTESTINAL TRACT

[76] Inventor: Leopold S. Kaplan, 8 Bradford Road, Edison, N.J. 08817

[21] Appl. No.: 677,242

[22] Filed: Apr. 15, 1976

[51] Int. Cl.² ........................... A61B 1/12; A61B 6/00
[52] U.S. Cl. ..................................... 128/2 A; 128/208
[58] Field of Search .............. 128/2 R, 2 A, 208, 272, 128/349 B, 222; 239/33; 215/11 B, 11 D

[56] References Cited
U.S. PATENT DOCUMENTS

| 3,470,869 | 10/1969 | Fenton et al. | 128/2 A |
| 3,749,312 | 7/1973 | Panzer | 128/2 A X |
| 3,905,361 | 9/1975 | Hewson | 128/349 B X |
| 3,937,224 | 2/1976 | Uecker | 128/349 B X |
| 3,972,326 | 8/1976 | Brawn | 128/208 X |
| 3,977,408 | 8/1976 | Mackew | 128/349 B |

Primary Examiner—Stephen C. Pellegrino
Attorney, Agent, or Firm—Lerner, David, Littenberg & Samuel

[57] ABSTRACT

A method and device for obtaining the type of gastric mucosal coating of a human being's upper gastrointestinal tract to enable a double-contrast study of said tract to be performed are disclosed. The method comprises the steps of providing an open-ended feed tube having first and second ends, and having a vent in the feed tube for the introduction of ambient air. The vent comprises venting means which are disposed in a direction towards the second end of the feed tube. The first end of the feed tube is disposed into a supply of contrast medium and the medium is ingested by sucking from the second end of the feed tube while simultaneously ingesting air through the venting means. The venting means define a vent opening which is large enough to permit ingestion of a sufficient amount of air to effect a desired degree of distention of the organs in the tract and small enough to prevent interference with the ingestion of the contrast medium, whereby the gaseous distention enhances the gastric mucosal coating and enables a double-contrast study of the organs to be performed.

15 Claims, 3 Drawing Figures

METHOD AND DEVICE FOR FACILITATING DOUBLE-CONTRAST STUDIES OF THE UPPER GASTROINTESTINAL TRACT

BACKGROUND OF THE INVENTION

To effect a standard gastrointestinal or "GI" study, a person is required to ingest a so-called "contrast medium". The contrast medium is opaque to X-rays and therefore the radiologist can, when the person stands before a fluoroscope, follow the flow of the medium through the digestive system. As the medium moves through the esophagus, stomach, and intestines, the radiologist can detect ulcers, tumors, or other abnormalities of the gastrointestinal tract. It is known that by first effecting a gastric mucosal coating with the contrast medium and distending the hollow organs of the upper gastrointestinal tract, specifically the esophagus, stomach and duodenum, it is possible to obtain double-contrast radiographs which permit much greater accuracy in the discovery of gastrointestinal problems than is possible in the standard or single-contrast "GI" study. Until now, the techniques for achieving gaseous distention of the organs, which is essential is obtaining clear, unobscured double-contrast views thereof, have involved the use of nasogastric intubation and ingestion of hypotonic drugs. It has also been reported that gaseous distention of the organs can be effected by the ingestion of effervescent granules which will release carbon dioxide within the person's gastrointestinal track such that distention of the organs will result. These effervescent granules, can be used in connection with hypotonic drugs as well.

Each of the methods for gaseous distention of the organs noted above are problematic in that a certain degree of discomfort to the patient is involved. In the case of nasogastric intubation, the discomfort experienced is quite apparent. Further, where hypotonic agents are used there is always uncertainty as to a person's reaction to such drugs.

It is an object of the present invention to provide a method and device for obtaining a gastric mucosal coating of the upper gastrointestinal tract with a contrast medium and gaseously distending the organs to enhance the coating and enable a double-contrast study to be performed, which is not accompanied by the drawbacks presently associated with the known methods described above.

SUMMARY OF THE INVENTION

The present invention relates to a method and device for preparing a person's gastrointestinal track so that a double-contrast study thereof can be effected. To this end, the present invention specifically relates to a method for obtaining a gastric mucosal coating of the esophagus, stomach and duodenum with a contrast medium and gaseously distending these organs to thereby enhance the coating and enable double-contrast radiographs to be obtained.

More specifically, the method of the present invention comprises providing an open-ended feed tube having first and second ends and providing a vent in the feed tube which is comprised of venting means being disposed in a direction toward the second end of the feed tube. The first end of the feed tube is placed in a supply of the contrast medium which is to be ingested and the medium is then sucked through the tube from the second end thereof. The construction of the feed tube and venting means is such that a mixture of air and the medium are simultaneously ingested. To this end, the venting means define a vent opening which is large enough to permit ingestion of sufficient air to effect distention of the organs but small enough to prevent interference with ingestion of the contrast medium through the feed tube.

The venting means through which air is introduced can be provided in the feed tube in a number of ways. Specifically, it can be provided by inserting a hypodermic needle into the feed tube or by inserting a separate tube therein. Alternatively, the venting means can be manufactured as an integral part of the feed tube itself. It may be desired, in certain instances, to utilize the device of the present invention for conducting standard single-contrast studies of the gastrointestinal tract. When such is the case, the venting means can be provided with means for closing the vent opening so that no air will be ingested along with the contrast medium.

The novel method and device of the present invention enables gaseous distention of the hollow organs in the upper gastrointestinal tract to be effected in a manner which avoids the discomfort and other drawbacks associated with the prior art methods. Further, the method disclosed is usable in conjunction with various known techniques for obtaining optimal mucosal coating for purposes of conducting double-contrast studies which techniques may involved certain physical maneuvering of the patient upon whom the study is being conducted, such as, for example, that disclosed in Vol. 117 of "Diagnostic Radiology", December 1975, in an article entitled "A Simple Method For Routine Double-Contrast Study Of The Upper Gastrointestinal Tract" by Dr. Igor Laufer.

DESCRIPTION OF DRAWINGS

For a more complete understanding of the invention, reference should be made to the following detailed description and drawings in which.

DETAILED DESCRIPTION

Figure 1:
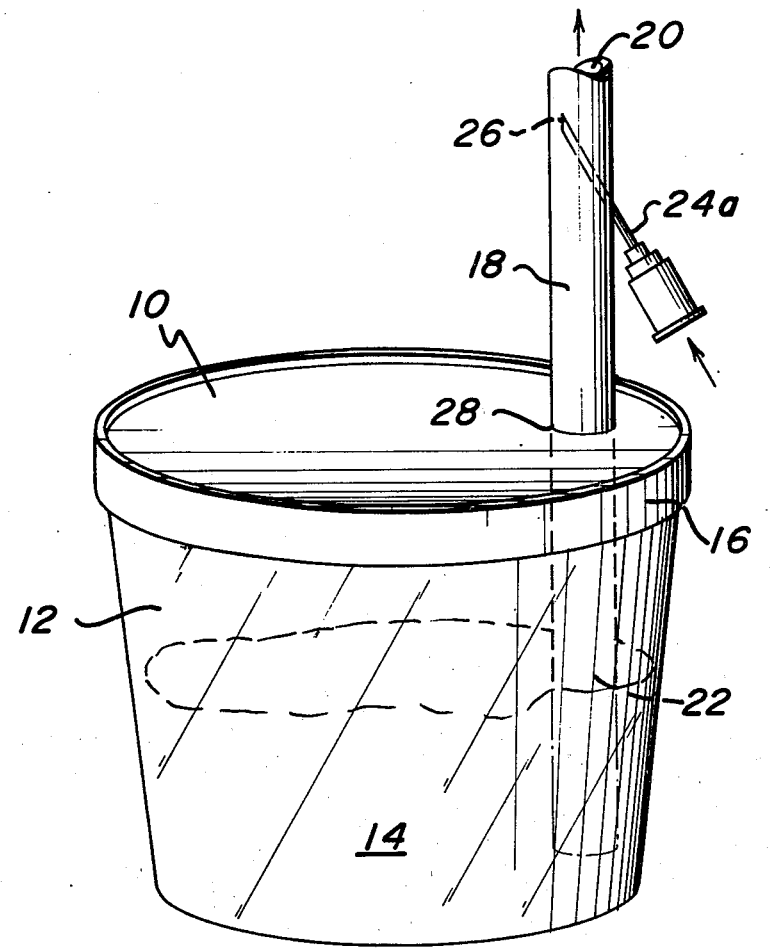
FIG. 1 is a front perspective view showing the device of the present invention.

Referring now to the drawings, 10 represents generally the novel device in accordance with the present invention. The device 10 includes container 12 which holds a supply of contrast medium 14 which is to be ingested into the gastrointestinal tract of a human being.

Container 12 is provided with cover member 16 having hole 28 therein. The feed tube 18 which has first and second ends 22 and 20, respectively, is of substantially the same configuration as the hole 28 so that the first end 22 of the feed tube 18 can be inserted through the hole 28 and disposed into the supply of contrast medium 14 as shown in FIG. 1. The contrast medium 14 is preferably barium sulfate. Typically, the barium sulfate will be supplied in powdered form and must be mixed with a quantity of water prior to ingestion.

Feed tube 18 is provided with venting means 24 which is disposed in a direction toward the second end 20 of the feed tube 18. It has been found that the venting means must be disposed in such a direction to enable air to be ingested when the contrast medium 14 is ingested by sucking on the second end 20 of the feed tube 18 while the first end 22 is disposed in the contrast medium 14.

Figure 2:
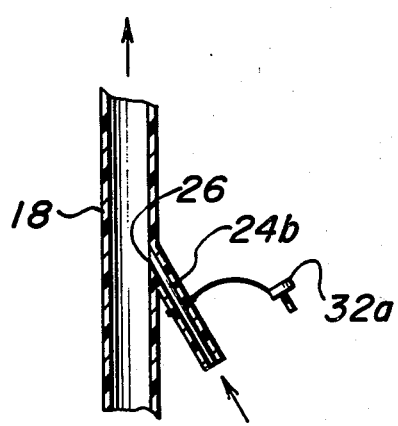
FIG. 2 is a sectional view showing an alternative embodiment for the feed tube and venting means of the present invention.
Figure 3:
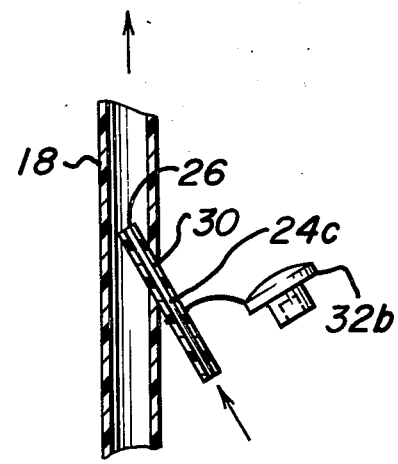
FIG. 3 is a sectional view of another embodiment of the feed tube and venting means of the present invention.

By reference to FIGS. 1, 2 and 3, it can be seen that the venting means 24 can be of three general types, i.e., the venting means can be provided by inserting a hypodermic needle 24a into the wall of feed tube 18 as shown in FIG. 1, or can be provided in the manner as shown in either FIGS. 2 or 3. In FIG. 2, the venting means 24b is formed integrally with the feed tube 18 during the manufacture thereof. Alternatively, as shown in FIG. 3, the venting means can comprise a separate tube 24c which is inserted into a hole 30 which has been formed in the side of feed tube 18.

Regardless of which embodiment of the venting means is utilized, it has been found that the vent opening which is defined by the venting means must be large enough to permit ingestion of a sufficient amount of air to effect a desired degree of distention of the organs and small enough to prevent intereference with ingestion of the contrast medium. Specifically, it has been found that the vent opening must have an inner diameter of at least 0.020 inches but no greater than 0.050 inches. More specifically, the use of an 18 gauge hypodermic needle which has an inner diameter of 0.033 inches as the venting means has been found to result in sufficient gaseous distention of the organs to obtain good gastric mucosal coating for purposes of conducting the study.

The device of the present invention may also be used to conduct standard single-contrast studies of a person's gastrointestinal tract. To this end, means 32 which are operable to close the vent opening can be provided. Such means can comprise plug means 32a, as shown in FIG. 2, or cap means 32b, as shown in FIG. 3. As can readily be appreciated, by closing the vent opening, only the contrast medium will be ingested upon sucking the medium through the feed tube 18.

When it is desired to prepare a person's gastrointestinal tract for purposes of conducting a double-contrast study thereof, in accordance with the present invention, the first end 22 of the feed tube 18 is inserted through the hole 28 in the cover member 16 of the container 12 and thus disposed in the supply of contrast medium 14 contained therein. With the vent 24 provided in the feed tube 18 as described hereinabove, the sucking of the medium through the feed tube from the second end 20 thereof results in a simultaneous ingestion of the fluid medium as well as air which enters through the venting means 24. As noted above, so long as the vent opening has been chosen within limits that are dictated by the desired degree of distention of the organs on the one hand and the avoidance of interference with ingestion of the contrast medium on the other hand, sufficient air will be ingested along with the contrast medium so that gaseous distention and coating of the desired degree will be accomplished.

As noted above, the device of the present invention can be used to effect the type of enhanced gastric mucosal coating which facilitates double-contrast studies of the upper gastrointestinal tract and, if desired, can be used in conjunction with physical maneuvering techniques as designed to optimize the mucosal coating such as described by Dr. Laufer in his article referred to above. Whether the device and method of the present invention are used alone or in conjunction with these other techniques, it is apparent that a relatively simple and efficient method for obtaining a good mucosal coating in conjunction with gaseous distention of the organs is involved which does not have associated therewith any of the physical discomfort that is characteristic of the prior art methods.

While the above invention has been described with a certain degree of particularity, it is to be understood that the present disclosure is made by way of example only and that numerous variations as may become apparent to those skilled in the art may be made without departing from the spirit and scope of the invention as hereinafter claimed.

What is claimed is:

1. A method for obtaining a gastric mucosal coating of the hollow organs in a human being's upper gastrointestinal tract with a contrast medium and gaseously distending said organs to enhance said coating and enable a double-contrast study of said tract to be performed, said method comprising the steps of providing an open-ended feed tube having first and second ends, providing a vent in said feed tube for the introduction of air; said vent comprising venting means intercommunicating with said feed tube means and being disposed at an angle less than 90° in a direction toward said second end of said feed tube such that air drawn through said venting means will intercept the flow of contrast medium through said feed tube within said feed tube at substantially said angle, said venting means further defining a vent opening having an inner diameter of from 0.020 inches to 0.050 inches, said vent opening being large enough to permit ingestion of sufficient air to effect a desired degree of distention of said organs and small enough to prevent interference with the flow of said fluid contrast medium through said feed tube; disposing said first end of said feed tube into said medium, and sucking on said second end of said feed tube to draw said medium through said feed tube while simultaneously drawing air through said venting means so that a mixture of air and said medium is ingested.

2. The method of claim 1 wherein said venting means comprises a hypodermic needle and said vent is provided in said feed tube by insertion of said needle into said feed tube.

3. The method of claim 1 wherein said venting means comprises tubular venting means and said vent is provided in said feed tube by forming a hole in said feed tube and inserting said separate tubular vent means into said hole.

4. The method of claim 1 wherein said venting means comprises tubular venting means and said vent is provided in said feed tube by forming said tubular venting means integrally with said feed tube.

5. The method of claim 1 wherein said contrast medium is barium sulfate.

6. A device for obtaining a gastric mucosal coating of the hollow organs in a human being's upper gastrointestinal tract with a contrast medium and gaseously distending said organs to enhance said coating and enable a double-contrast study of said tract to be performed, said device comprising open-ended feed tube means having first and second ends, and venting means in intercommunication with said feed tube means disposed at an angle less than 90° in a direction toward said second end of said feed tube means such that air drawn through said venting means will intercept the flow of contrast medium through said feed tube within said feed tube at substantially said angle, said venting means further defining a vent opening having an inner diameter of from 0.020 inches to 0.050 inches said vent opening being large enough to permit ingestion of sufficient air to effect a desired degree of distention and small enough to prevent interference with the flow of said fluid contrast medium when said first end of said feed tube means is disposed into a supply of said contrast medium and when said medium is drawn through said feed tube means by sucking on said second end of said feed tube while simultaneously drawing air through said venting means so that a mixture of air and said contrast medium is ingested.

7. The device of claim 6 wherein said venting means comprises a hypodermic needle inserted into said feed tube means.

8. The device of claim 6 wherein said venting means comprises a separate tubular venting means inserted into said feed tube means.

9. The device of claim 6 wherein said venting means comprises tubular venting means formed integrally with said feed tube means.

10. The device of claim 6 further comprising a container with a supply of contrast medium therein and means for combining said feed tube means with said container.

11. The device of claim 10 wherein said last mentioned means comprises a cover on said container having an aperture therein, said first end of said feed tube means passing through said aperture and disposed in said supply of contrast medium.

12. The device of claim 10 wherein said contrast medium is barium sulfate.

13. The device of claim 6 wherein said venting means further comprises means for closing said vent opening.

14. The device of claim 13 wherein said means for closing comprises plug means.

15. The device of claim 13 wherein said means for closing comprises cap means.

* * * * *